(12) United States Patent
Schulz et al.

(10) Patent No.: US 12,653,988 B2
(45) Date of Patent: Jun. 16, 2026

(54) ALBARRAN DEFLECTOR

(71) Applicant: OLYMPUS WINTER & IBE GMBH, Hamburg (DE)

(72) Inventors: Kevin Schulz, Wilstedt (DE); Irina Schmuck, Heide (DE); Bastian Schroeder, Hamburg (DE); Andreas Ruehs, Ahrensburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 569 days.

(21) Appl. No.: 18/116,650

(22) Filed: Mar. 2, 2023

(65) Prior Publication Data

US 2023/0277050 A1     Sep. 7, 2023

Related U.S. Application Data

(60) Provisional application No. 63/315,709, filed on Mar. 2, 2022.

(51) Int. Cl.
| | |
|---|---|
| *A61B 1/015* | (2006.01) |
| *A61B 1/12* | (2006.01) |
| *A61M 25/01* | (2006.01) |
| *A61B 17/00* | (2006.01) |

(52) U.S. Cl.
CPC .................... *A61M 25/0147* (2013.01); *A61B 2017/00323* (2013.01)

(58) Field of Classification Search
CPC ... A61B 1/00064–1/0016; A61B 1/005–1/018; A61B 1/12–1/128; A61B 1/227–1/317;
A61B 17/3421; A61B 17/3423; A61B 2017/00323; A61B 2017/320084; A61B 2218/002; A61B 1/00135; A61B 1/015; A61B 1/05; A61B 1/125; A61B 1/126; A61B 1/00098; A61M 25/0147
See application file for complete search history.

(56) References Cited

U.S. PATENT DOCUMENTS

| | | | |
|---|---|---|---|
| 2016/0150946 A1 | 6/2016 | Tsumaru et al. | |
| 2018/0125567 A1* | 5/2018 | Ciccone | A61B 18/149 |
| 2020/0113426 A1 | 4/2020 | Ito et al. | |
| 2020/0323591 A1 | 10/2020 | Ransome | |
| 2020/0367732 A1* | 11/2020 | Yamaya | A61B 1/00098 |

FOREIGN PATENT DOCUMENTS

| | | |
|---|---|---|
| DE | 10 2016 003 175 A1 | 9/2017 |
| DE | 10 2016 122 477 A1 | 5/2018 |
| DE | 10 2017 117 385 A1 | 2/2019 |
| EP | 3861918 A1 | 8/2021 |

* cited by examiner

*Primary Examiner* — Kathleen S Holwerda
(74) *Attorney, Agent, or Firm* — Oliff PLC

(57) ABSTRACT

An Albarran deflector can be cleaned or reconditioned particularly thoroughly. This is achieved in that at least one flushing port is arranged on a drive body of the Albarran deflector. During cleaning or reconditioning, a flushing line can be connected to this flushing port. This defined access to the interior of the drive body or gear space allows targeted introduction of the flushing fluid.

10 Claims, 3 Drawing Sheets

ALBARRAN DEFLECTOR

The invention concerns an Albarran deflector according to the preamble of claim 1.

Albarran deflectors are used as support in operations or treatments with surgical instruments, such as for example endoscopes, resectoscopes, cystoscopes or similar. An Albarran deflector may be used for example to deflect flexible forceps inside a patient in a targeted and controlled fashion. For this, exactly like an endoscope for example, the Albarran deflector has a rod-like or tubular shaft, a distal end of which must be guided into the patient's body. At the proximal end of the Albarran deflector outside the patient, the shaft is connected to a main body. Via this main body, instruments or tools such as for example an optic, wires or similar can be guided into the patient through the shaft via various openings or ports.

At the distal end of the shaft, the Albarran deflector has a lever, known as an Albarran lever. This lever is designed movably and can be actuated or pivoted via a toggle on the main body. For this, the lever is mechanically coupled to the toggle along the shaft. This mechanical coupling may comprise either a rod or a traction wire. Usually, the lever is connected to the toggle via two traction wires. It is conceivable that both traction wires serve similarly to pivot the lever forward and back, or the two traction wires may implement different movements of the lever via the toggle.

For reliable operation of the Albarran lever, the traction wires inside the main body, in a drive body or gear space therein, must be clamped to a traction wire carrier. The traction wire carrier is mounted on the shaft so as to be movable along the longitudinal axis of the Albarran deflector. The rotational movement of the toggle is converted in the gear space into a linear movement of the traction wire carrier. In this way, by twisting the toggle, the traction wire carrier and hence also the traction wires can be moved forward and back parallel to the shaft, whereby the lever at the distal end of the shaft is rotated about an axis. The gear mechanism is arranged in the gear space and is sealed towards outside by grease, mastic or seals. With this design, the gear space has no access to or contact with the patient or user.

To prepare the Albarran deflector or main body for re-use, it is essential that all, in particular internal components can be flushed, disinfected and sterilized. The sealing elements such as grease, mastic and other seals suffer during the various reconditioning processes (ultrasound bath, mechanical cleaning, sterilization in autoclave). During these processes, the grease can be washed out, the mastic become friable and the seals fatigued. The previously sealed gear space can thus lose its tightness during the reconditioning processes. Thus, during the operation, fluids can enter the gear space and permanently contaminate this. This contamination can only be removed with great effort. It cannot be excluded that, after reconditioning of the instrument, some of the contamination remains in the gear space. There is therefore a danger that, on next use of the Albarran deflector, the residual fluid may emerge from the gear space and lead to a serious health risk to the patient or operator. Without being able to ensure the necessary thoroughness in reconditioning, certain surgical instruments, such as the Albarran deflector described herein and its components, are not reusable. Offering or using such complex instruments as single-use instruments is however too cost-intensive.

The invention is based on the object of creating an Albarran deflector which can be cleaned or reconditioned particularly thoroughly.

This object is achieved by the features of claim 1. Accordingly, it is provided that at least one flushing port is arranged on the drive body of the Albarran deflector. A flushing line can be connected to this flushing port during cleaning or reconditioning. Because of this defined access, the flushing fluid—which may be provided with a cleaning agent—may be introduced in targeted fashion into the interior of the drive body or gear space. The gear space and the components arranged in the gear space, such as for example the traction wire carrier, gear mechanism and traction wires, can thus be cleaned in a very thorough fashion. The flushing fluid may leave the gear space again through a further opening of the drive body.

A particularly preferred exemplary embodiment of the invention provides that the flushing port encloses an acute angle with the shaft pointing in the distal direction of the Albarran deflector. This relative angular position causes the flushing fluid to flow obliquely into the gear space in the proximal direction. It has been shown that this oblique introduction of flushing fluid allows the interior of the gear mechanism and all components mounted therein to be flushed in a highly efficient and thorough fashion. In order to leave the gear space again, the flushing fluid must change its flow direction inside the gear space. The resulting turbulence and pressure differences inside the flushing stream ensure that any contamination or residue is flushed out particularly thoroughly.

The invention provides in particular that the flushing port is arranged directly above the traction wire carrier on the drive body, so that the flushing fluid stream hits the in particular wedge-shaped or trapezoid traction wire carrier and is divided into two part streams. This division of the flushing stream may ensure that all surfaces inside the gear space are reached. This avoids leaving unflushed dead volumes within the drive body.

A further advantageous exemplary embodiment of the present invention may provide that at least one inner wall of the gear space is formed convex. This inner wall may preferably be an inner wall of the gear space opposite the flushing port. In the exemplary embodiment illustrated and described herein, the inner wall of the gear space is convex in the proximal direction, or concave in the distal direction. With this design of the inner wall, the flushing fluid flowing through the flushing port into the gear space is reflected particularly efficiently at the inner wall having a convex curve in the proximal direction. The outwardly convex design of at least one wall of the gear space allows a particularly advantageous flushing of all components arranged inside the gear space. Also, this curvature allows local increases in the flow speed, whereby because of the resulting pressure difference, a particularly thorough cleaning of all surfaces can be achieved.

Preferably, the main body has an outlet opening at its distal end, in particular parallel to the shaft. This outlet opening, like the flushing port, is oriented in the distal direction. Thus the flushing stream inside the main body must undergo a direction change of at least almost 180°. This necessary direction reversal of the flushing fluid has a particularly advantageous effect on the cleaning action of the flushing fluid.

Preferably, it may be provided that the outlet opening is larger than or the same size as the flushing port. This difference in dimensions of the openings allows a pressure gradient to be set, which has an advantageous effect on the flow speed of the flushing fluid.

A further advantageous exemplary embodiment of the invention may provide that the outlet opening is formed tubular and tapers in its diameter in the distal direction. This taper causes an increase in flow speed, whereby a type of suction effect is created inside the drive body. Thus even larger contaminants, such as for example particles, can be efficiently removed from the gear space.

Furthermore, according to the invention, it is conceivable that at least one, preferably two closable access points are arranged on the main body. These access points may, during the operation, serve for introduction of further instruments or tools in the shaft. Similarly, these access points may be used to serve as an outlet opening for the flushing fluid. Similarly, it is conceivable that an additional flushing port is provided, leading into the gear space via the access points.

It is conceivable that the flushing port is formed as a Luer lock connection. Thus corresponding lines or hoses or other fluid-containing means may be connected to the flushing port in a particularly simple and secure fashion. During the operation, it is conceivable that the flushing port can be closed by a sealing cap, a cover, a valve, a flap or similar. This may prevent both fluid from emerging from the gear space and also fluid or other objects from being able to enter the gear space. During the operation, all openings are closed by these means. No further sealing means are required. These means can easily be removed for cleaning or reconditioning.

A preferred exemplary embodiment of the present invention is explained in more detail below with reference to the drawing. In the drawing.

Figure 1:
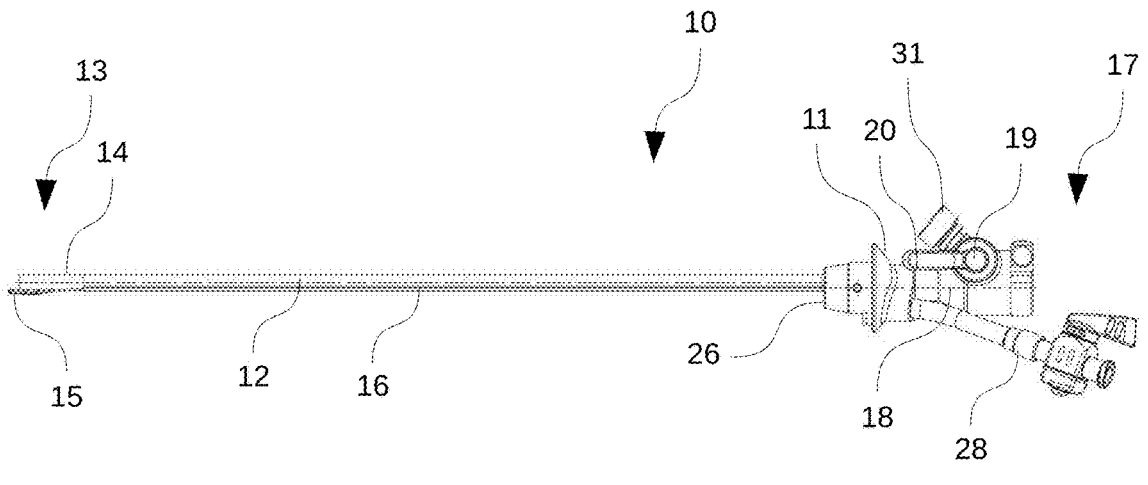
FIG. 1 shows a side view of an Albarran deflector.

FIG. 1 shows a possible exemplary embodiment of an Albarran deflector 10. It is expressly pointed out that the scope of protection of the present application is not restricted to this exemplary embodiment. It is rather provided that further embodiments of the invention are included in the scope of protection.

The Albarran deflector 10 substantially consists of a main body 11 and a shaft 12 mounted on the main body 11. The shaft 12 is tubular and, for treatment of persons, a distal end 13 thereof is introduced into the body of the person. Various medical or surgical instruments may be guided through the shaft 12. An Albarran lever 15 is movably arranged on an outer wall 14 at the distal end 13 of the shaft 12. During treatment, this lever 15 serves as an aid for the operator for the performance of further treatment steps. The lever 15 is mounted so as to be pivotable about an axis. The lever 15 can be actuated via traction wires 16 for movement about its axis.

The traction wires 16 run parallel to the shaft 12 from the lever 15 to the proximal end 17 of the Albarran deflector 10. For this, the traction wires 16 are guided through the main body 11 and attached to a traction wire carrier 21 in a drive body 18 of the main body 11. To operate the lever 15, the drive body 18 has a toggle 19 with two actuating means 20. By rotating these actuating means 20, the traction wire carrier 21 and hence also the traction wires 16 can be moved forward and back linearly along the shaft 12, whereby the lever 15 executes a pivot movement. To convert the rotational movement into a translational movement, the traction wire carrier 21 has an elongate bore 22. A pin 23 of the toggle 19 engages in this elongate bore 22, wherein this pin 23 is moved eccentrically to the rotational axis of the toggle 19. This combination of bore 22 and pin 23 is also known as a gear mechanism, so the interior of the drive body 18 is also described as a gear space 24.

Figure 2:
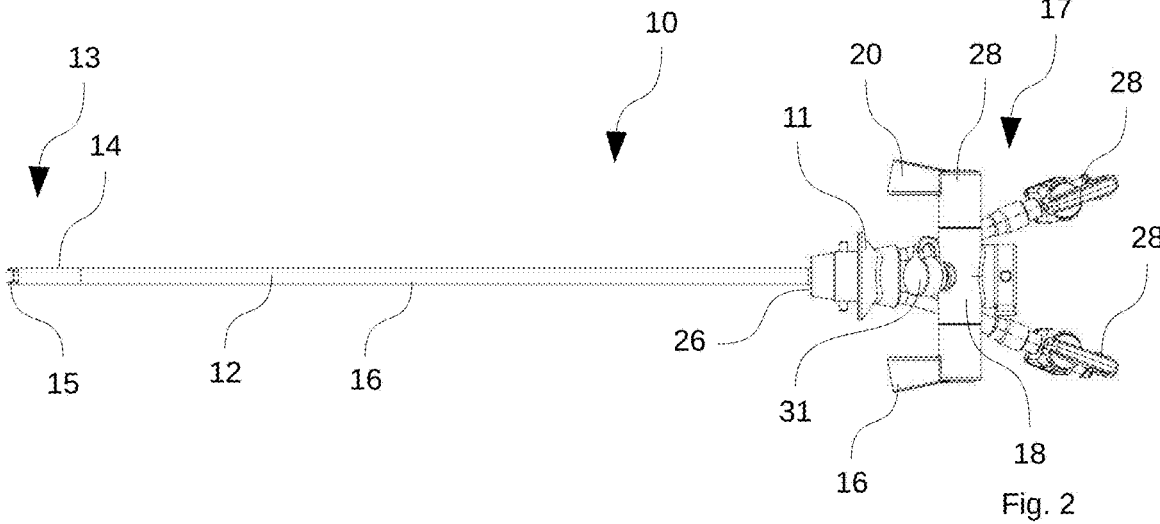
FIG. 2 shows a view of the Albarran deflector from FIG. 1.
Figure 3:
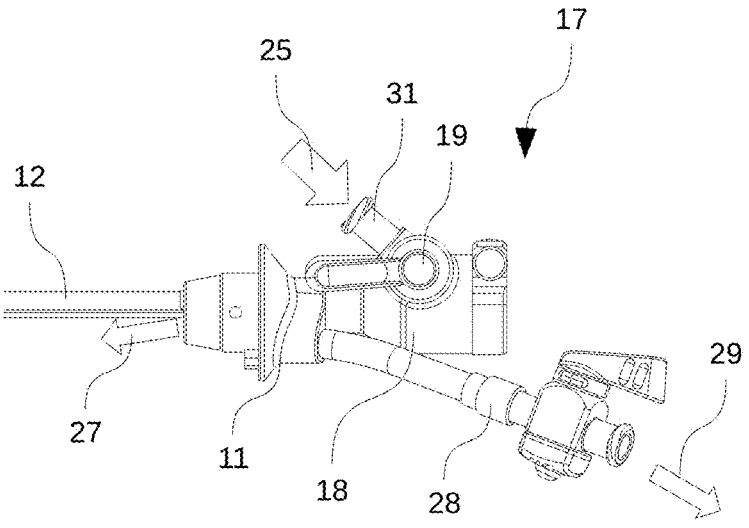
FIG. 3 shows an illustration of a proximal end of the Albarran deflector.

In order to be able to clean the Albarran deflector 10 and in particular the main body 11, a flushing port 31 is arranged on the drive body 18. This flushing port 31 encloses an acute angle with the shaft 12 and is thus tilted in the direction of the distal end 13 of the shaft 12 (FIGS. 1 and 2). A flushing fluid can be conveyed through this flushing port 31 into the drive body 18 in the arrow direction 25 (FIG. 3). The fluid can leave the main body 11 again for example at a distal end 26 in the arrow direction 27, or be discharged or extracted via two additional access points 28 in the arrow direction 29. Whereas the flushing port 31 can be fitted with a cover for closing the opening, in the exemplary embodiment of the Albarran deflector 10 shown here, the access points 28 may each have a valve. The flushing fluid can be actively extracted from the main body 11 by a pump via the access points 28. Thus the flushing of the main body 11 or entire Albarran deflector 10 can be carried out in a particularly thorough fashion.

Figure 4:
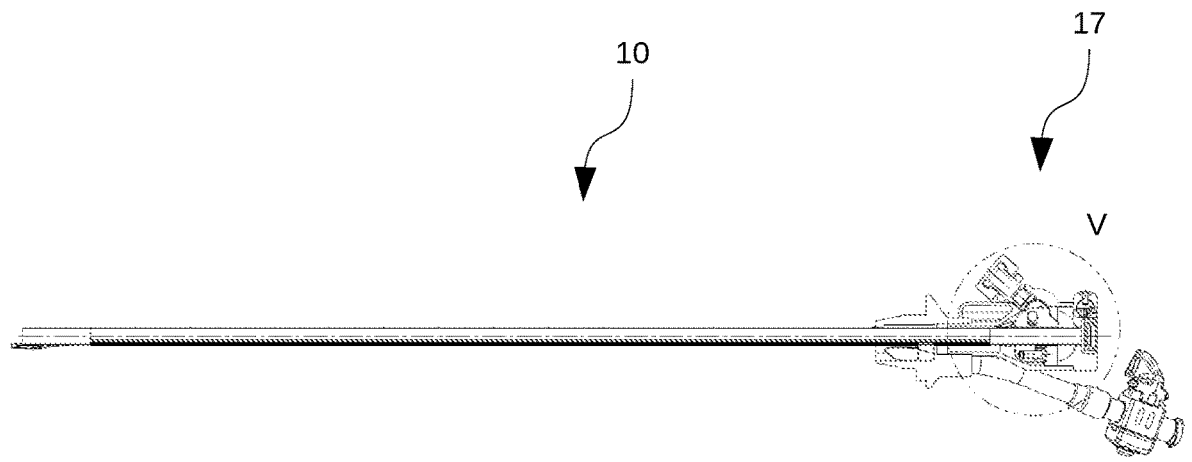
FIG. 4 shows a sectional illustration through the Albarran deflector from FIG. 1.
Figure 5:
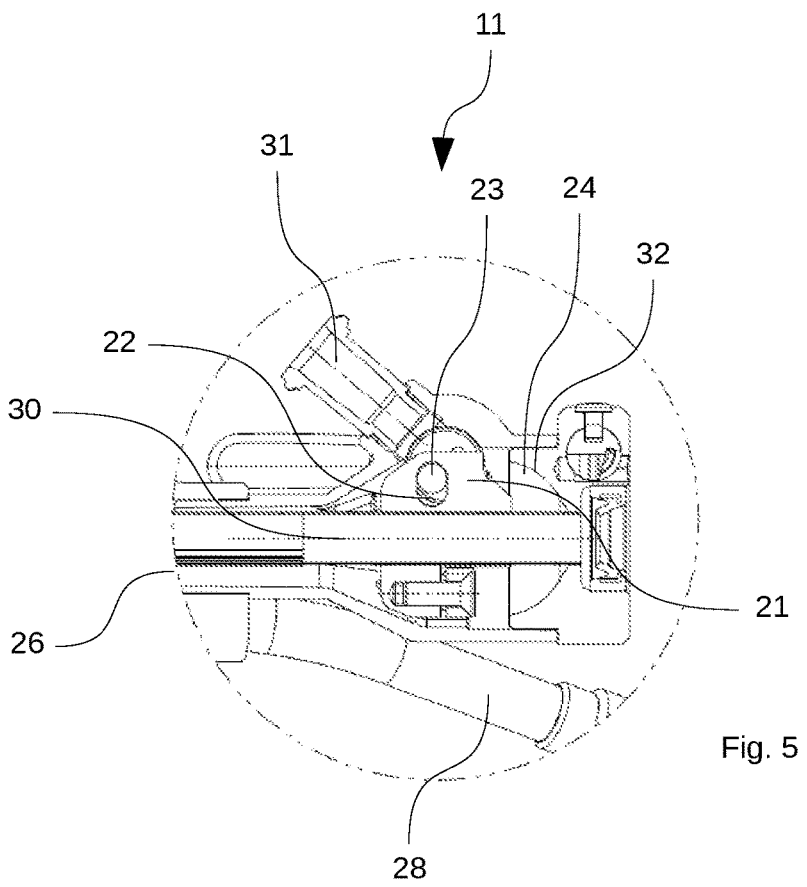
FIG. 5 shows an enlarged extract of the proximal portion of the Albarran deflector from FIG. 4.

By the inflow of flushing fluid into the gear space 24, both the inner walls of the gear space 24 and the surfaces of an inner shaft 30 or an optic tube and the traction wire carrier 21 are cleaned. This cleaning takes place particularly efficiently thanks to the dimensioning of the diameter of the flushing port 31 and the distal end 26 or the outlet and the access points 28. It is an essential feature of the invention that a proximal inner wall 32 of the gear space 24 is formed convex in the proximal direction (FIGS. 4, 5). This convex curvature of the inner wall 32 deflects the flushing fluid, flowing into the gear space 24 through the flushing port 31, in the opposite direction. Because of this deflection, all surfaces inside the gear space 24 are flushed in a very efficient fashion. Also, the flushing fluid is conducted directly back in the direction of the distal end 26 of the main body 11.

Figure 6:
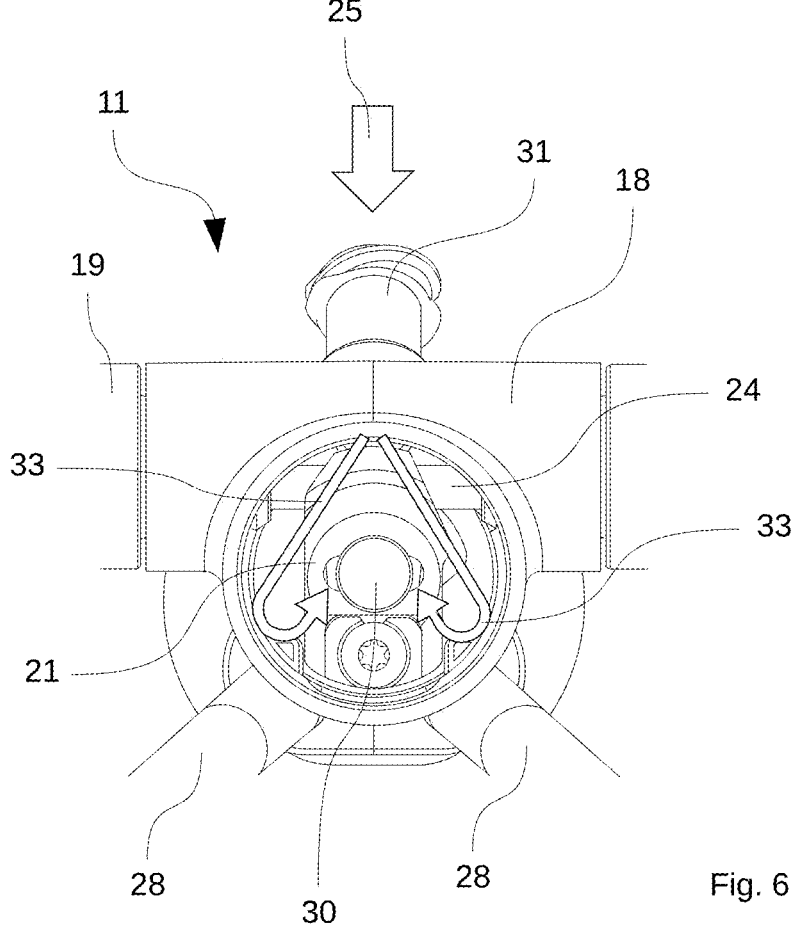
FIG. 6 shows a view into a main body of the Albarran deflector.

As shown in FIG. 6, the traction wire carrier 21 may have a trapezoid cross-section. Thanks to this shape, the flushing stream entering the gear space 24 through the flushing port 31 is divided into two part streams 33, so that the interior of the drive body 18 is evenly flushed.

In order to clean the Albarran deflector 10, and in particular the gear space 24, a hose may be coupled to the flushing port 31, which may also be configured as a Luer lock. Via this hose, the flushing fluid may be conveyed into the gear space 24 under a specific pre-pressure. After the end of the cleaning process and when the Albarran deflector 10 is sufficiently dry, the openings, and in particular the flushing port 21 and the distal end 26 main body 11, are closed again, so that in the following operation no foreign bodies may enter the gear space 24 or no foreign bodies can pass from the gear space 24 into the patient.

LIST OF REFERENCE SIGNS

10 Albarran deflector
11 Main body
12 Shaft
13 Distal end
14 Outer wall
15 Lever
16 Traction wire 17 Proximal end
18 Drive body
19 Toggle
20 Actuating means
21 Traction wire carrier
22 Bore
23 Pin
24 Gear space
25 Arrow direction
26 Distal end
27 Arrow direction
28 Access point
29 Arrow direction
30 Inner shaft
31 Flushing port
32 Inner wall
33 Part stream

The invention claimed is:

1. An Albarran deflector comprising:
a tubular shaft:
an Albarran lever arranged at a distal end of the tubular shaft; and
a main body with a drive body arranged at a proximal end of the tubular shaft, wherein:
 the Albarran lever is movable on the drive body by a toggle via at least one traction wire which is attached to a traction wire carrier inside a gear space of the drive body;
 a flushing port is arranged on the drive body; and
 at least one inner wall of the gear space is formed convex in a proximal direction, such that the at least one inner wall of the gear space is configured to deflect fluid into the gear space towards a distal end of the main body.

2. The Albarran deflector as claimed in claim 1, wherein the flushing port encloses an acute angle with the tubular shaft pointing in a distal direction of the Albarran deflector.

3. The Albarran deflector as claimed in claim 1, wherein the flushing port is arranged directly above the traction wire carrier on the drive body so that a flushing fluid stream hits the traction wire carrier and is divided into two-part streams.

4. The Albarran deflector as claimed in claim 1, wherein the main body has an outlet opening at its distal end.

5. The Albarran deflector as claimed in claim 4, wherein the outlet opening is larger than or a same size as the flushing port.

6. The Albarran deflector as claimed in claim 4, wherein the outlet opening is formed tubular and tapers in its diameter in a distal direction.

7. The Albarran deflector as claimed in claim 1, wherein at least one closable access point is arranged on the main body.

8. The Albarran deflector as claimed in claim 1, wherein the flushing port is formed as a Luer lock connection.

9. The Albarran deflector as claimed in claim 1, wherein the flushing port can be closed by a sealing cap, a cover, a valve, or a flap.

10. The Albarran deflector as claimed in claim 1, wherein the traction wire carrier is wedge-shaped.

* * * * *